(12) United States Patent
Park

(10) Patent No.: US 9,624,474 B2
(45) Date of Patent: Apr. 18, 2017

(54) METHOD OF SEPARATING TARGET CELL IN BIOLOGICAL SAMPLE

(71) Applicant: SAMSUNG ELECTRONICS CO., LTD., Suwon-si, Gyeonggi-do (KR)

(72) Inventor: Jong-myeon Park, Yongin-si (KR)

(73) Assignee: SAMSUNG ELECTRONICS CO, LTD., Suwon-si (KR)

(*) Notice: Subject to any disclaimer, the term of this patent is extended or adjusted under 35 U.S.C. 154(b) by 254 days.

(21) Appl. No.: 13/949,320

(22) Filed: Jul. 24, 2013

(65) Prior Publication Data

US 2013/0309662 A1 Nov. 21, 2013

Related U.S. Application Data

(63) Continuation-in-part of application No. 13/302,678, filed on Nov. 22, 2011, now abandoned.

(30) Foreign Application Priority Data

Dec. 1, 2010 (KR) ........................ 10-2010-0121333

(51) Int. Cl.
| | |
|---|---|
| C12N 5/00 | (2006.01) |
| C12N 5/02 | (2006.01) |
| C12N 5/09 | (2010.01) |
| C07K 16/30 | (2006.01) |

(52) U.S. Cl.
CPC ............ *C12N 5/0693* (2013.01); *C07K 16/30* (2013.01)

(58) Field of Classification Search
None
See application file for complete search history.

(56) References Cited

U.S. PATENT DOCUMENTS

| 5,474,687 A | 12/1995 | Van Vlasselaer |
| 5,593,848 A | 1/1997 | Levine et al. |
| 5,840,502 A * | 11/1998 | Van Vlasselaer ............ 435/7.21 |
| 2003/0124719 A1 | 7/2003 | Woodside |
| 2004/0265994 A1* | 12/2004 | Brahmbhatt et al. ......... 435/325 |
| 2009/0081689 A1* | 3/2009 | Yamanishi et al. ............... 435/6 |

FOREIGN PATENT DOCUMENTS

| KR | 1020010052168 A | 6/2001 |
| KR | 1020060018474 A | 3/2006 |
| KR | 1020100027390 A | 3/2010 |

OTHER PUBLICATIONS

Patel et al. et al. (Clinica Chimica Acta 240 (1995) 187-193.*
U.S. Appl. No. 13/302,678, filed Nov. 22, 2011.
Ficoll PM 70, Ficoll PM 400, data file 18-1158-27, pp. 1-6, Amersham Biosciences, (2001).
Müller, V. et al., Circulating Tumor Cells in Breast Cancer: Correlation to Bone Marrow Micrometastases, Heterogeneous Response to Systemic Therapy and Low Proliferative Activity, *Clin Cancer Res.*, 11(10): 3678-3685 (2005).
Park et al., Highly Efficient Assay of Circulating Tumor Cells by Selective Sedimentation with a Density Gradient Medium and Microfiltration from Whole Blood, *Analytical Chemistry*, 84: 7400-7407(2012).
Shortman, K., The Separation of Different Cell Classes from Lymphoid Organs: II. The Purification and Analysis of Lymphocyte Populations by Equilibrium Density Gradient Centrifugation, *Aust. J. exp. Biol. med. Sci.* 46: 375-396 (1968).
European Patent Office, Extended European Search Report in European Patent Application No. 11191563.3 (Feb. 16, 2012).

* cited by examiner

*Primary Examiner* — Michail Belyavskyi
(74) *Attorney, Agent, or Firm* — Leydig, Voit & Mayer, Ltd.

(57) ABSTRACT

Provided is a method of separating a rare cell from a sample comprising incubating a sample comprising a rare cell and a second cell with a particle comprising a moiety capable of binding to the rare cell to form a complex comprising the particle and the rare cell; applying the mixture to a medium having a density gradient; and centrifuging the mixture to separate the complex from the second cell.

13 Claims, 14 Drawing Sheets

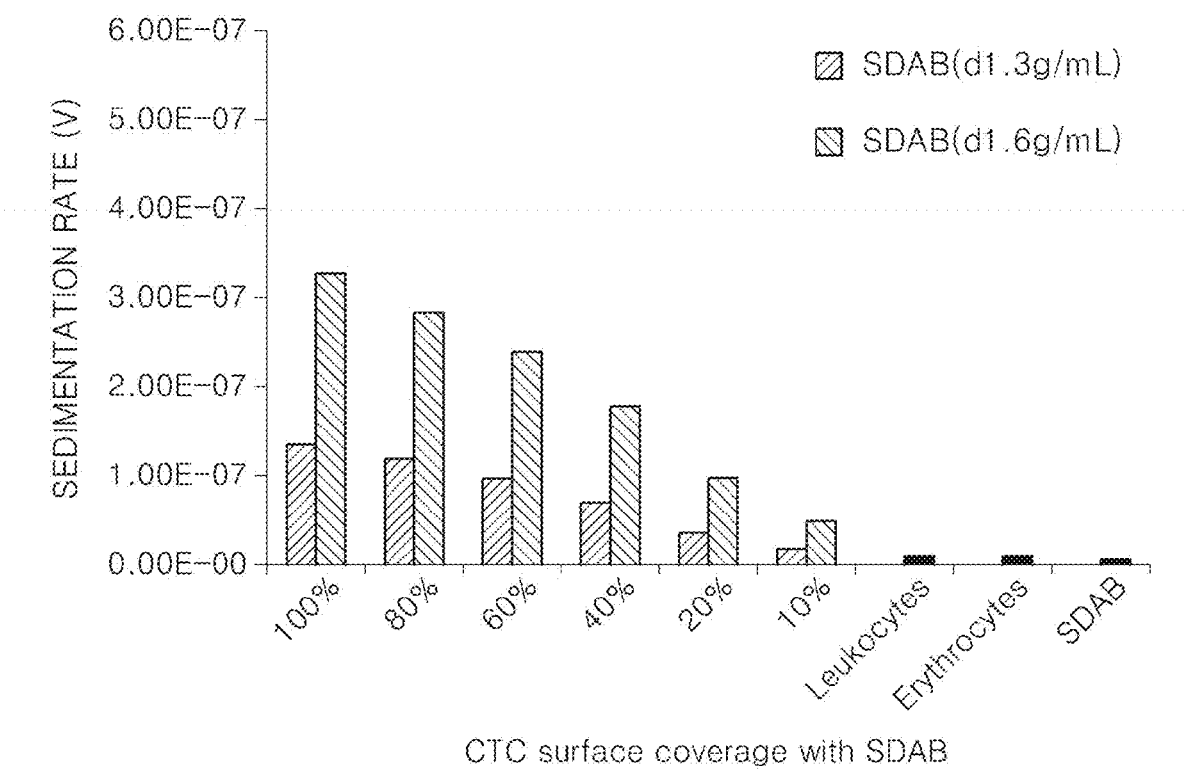

METHOD OF SEPARATING TARGET CELL IN BIOLOGICAL SAMPLE

CROSS-REFERENCE TO RELATED APPLICATIONS

This application is a continuation-in-part of U.S. patent application Ser. No. 13/302,678, filed on Nov. 22, 2011, which claims the benefit of Korean Patent Application No. 10-2010-0121333, filed on Dec. 1, 2010, and Korean Patent Application No. 10-2011-0111416, filed on Oct. 28, 2011, the disclosures of which are incorporated herein in their entirety by reference.

BACKGROUND

1. Field

The present disclosure relates to methods of separating a target cell in a biological sample.

2. Description of the Related Art

The majority of deaths associated with malignant tumors are due to the metastasis of primary tumor cells to tissues and organs distant from the initial tumor. Accordingly, early diagnosis of metastasis is a critical factor for the survival of a cancer patient, and early diagnosis of a tumor and monitoring of tumor growth are considered to be very important factors for successful treatment of a cancer patient. Cancer diagnosis usually involves diagnosis techniques related to histopathology. A histopathological diagnosis technique is a method of using a tissue sample from a living subject to diagnose cancer. Such a histopathological approach allows a tumor cell to be directly observed. However, the histopathological approach may be inaccurate in determining whether there is a tumor, since only data about the particular tissue sample site is obtained. Thus it can be difficult to know whether a tumor has metastasized to another site. For this reason, the applicability of the histopathological diagnosis technique in diagnosing and monitoring tumors may be limited.

Circulating tumor cells (CTCs) may be found in a patient before a tumor is initially detected. Accordingly, CTCs may play an important role in early diagnosis and prognosis of cancers. In addition, because cancer usually metastasizes through the blood, a CTC may be a marker for determining whether cancer has metastasized. Even after cancer cells have been removed by surgery, CTCs may still be found. In this case, this may indicate that cancer may reoccur. However, very small numbers of these CTCs are found in blood. It is thus very difficult to detect and quantify CTCs. Accordingly, there remains a need for a diagnostic method that is highly sensitive with respect to detection of CTCs, cancer cells, or cancer stem cells in a patient.

The related art discloses a method of separating red blood cells, white blood cells, circulating cancer cells, and serum. However, white blood cells and circulating cancer cells are not separated from each other and exist as a mixture when the technology is used, and thus the method is disadvantageous in that the separation efficiency of white blood cells and circulating cancer cells is theoretically limited.

Other related art discloses cell margination and multi-orifice separation based on the principles of fluid dynamics. The former is a technology whereby the number of small cells, such as red blood cells, is decreased and the number of other cells is increased using a phenomenon which occurs in actual blood vessels in which small particles gather in the inner part of the blood vessels and large particles move outside. The latter is a principle whereby a channel along which fluid flows has an expanded tube section to gather large particles and small particles outside and in the middle of the channel, respectively, according to Reynolds number. However, it is difficult to selectively separate a desired target cell from actual blood using this principle, and there is limitation in treating a volume of several ml because the fluid flow rate is slow. However, it is necessary to dilute a fluid by several hundred times in order to control the Reynolds number, and thus there is a limitation in that samples of several hundred ml should be actually treated.

Accordingly, although the related art may be used, there still remains a need for a method of efficiently separating a target cell in a biological sample.

SUMMARY

Provided are methods of separating a rare cell from a sample. In an embodiment, the method includes contacting a biological sample comprising incubating a sample which includes a rare cell and a second cell, and a particle including a moiety capable of binding to the rare cell to form a complex of the particle and the rare cell; and performing centrifugation on the incubated mixture to separate a fraction including the complex of the particle and the rare cell.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which:

FIG. 5A shows comparison of sedimentation rates for cell-SDABs (solid lines) and hematopoietic cells (dashed lines). FIG. 5B shows ratio of the sedimentation rate between cell-SDABs and leukocytes.

FIG. 6B is a graph showing sedimentation rates versus CTC surface coverage with SDAB when the CTC has a 10 μm diameter.

DETAILED DESCRIPTION

Figure 1:
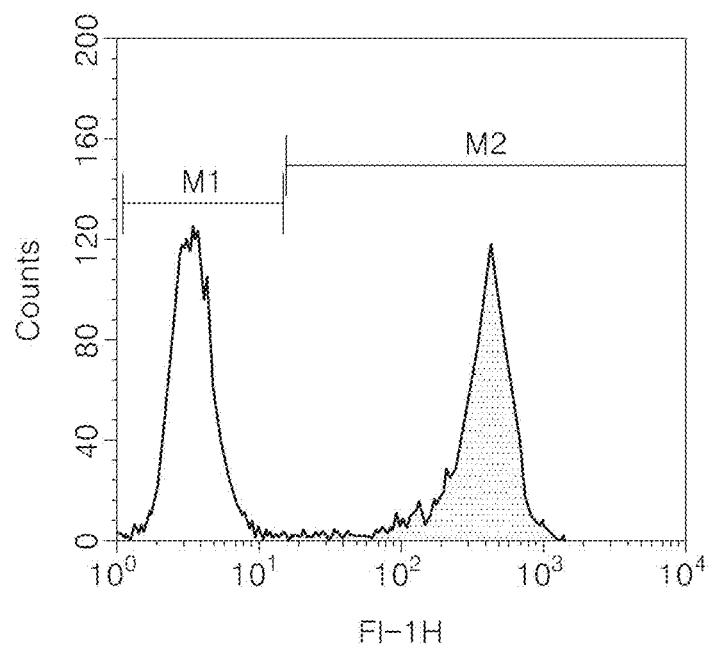
FIG. 1 is a graph that illustrates results of flow cytometric analysis of Human EpCAM/TROP1 Fluorescein MAb (anti-EPCAM MAb).

According to an aspect of the present invention, a method of separating a target cell from a biological sample includes incubating a sample which includes a rare cell and a second cell, and a particle including a moiety capable of binding to the rare cell to form a complex of the particle and the rare cell; and performing density gradient centrifugation on the incubated mixture to separate a fraction including the complex of the particle and the rare cell.

The method may include incubating a sample which includes a rare cell and a second cell, and a particle including a moiety capable of binding to the rare cell to form a complex of the particle and the rare cell.

The sample may include a rare cell and a second cell. For example, the sample may be a biopsy sample, a tissue sample, a cell suspension including a separated cell suspended in a liquid medium, a cell culture, or any combinations thereof. The sample may be blood, marrow fluid, saliva, lachrymal fluid, urine, semen, mucous fluid, or any combinations thereof.

The rare cell may be derived from blood, marrow fluid, saliva, lachrymal fluid, urine, semen, mucous fluid, or any combination thereof. As used herein, the term "rare cell" is interchangeable with the term "target cell". The rare cell may be present in the sample in a concentration of 1-100 cells/ml, 1-90 cells/ml, 1-80 cells/ml, 1-70 cells/ml, 1-60 cells/ml, 1-50 cells/ml, 1-40 cells/ml, 1-30 cells/ml, 1-20 cells/ml or 1-10 cells/ml. The rare cell may be a circulating tumor cell (CTC), endothelial cell, circulating tumor microemboli (CTM) stem cell, undifferentiated precursor cell, T lymphocyte, B lymphocyte, dendritic cell, or any combination thereof. The cancer cell or tumor cell may be a bladder cancer cell, breast cancer cell, cervical cancer cell, cholangiocarcinoma cancer cell, colorectal cancer cell, endometrial cancer cell, esophageal cancer cell, gastric cancer cell, head and neck cancer cell, kidney cancer cell, liver cancer cell, lung cancer cell, nasopharyngeal cancer cell, ovarian cancer cell, pancreatic cancer cell, gallbladder cancer cell, prostate cancer cell, thyroid cancer cell, osteosarcoma cell, synovial sarcoma cell, rhabdomyosarcoma cell, synovial sarcoma cell, Kaposi's sarcoma cell, leiomyosarcoma cell, malignant fibrous histocytoma cell, fibrosarcoma cell, adult T-cell leukemia cell, lymphoma cell, multiple myeloma cell, glioblastoma/astrocytoma cell, melanoma cell, mesothelioma cell, Wilms' tumor cell, or combination thereof.

The second cell is different from the rare cell, and may be any cell intended to be separated from the rare cell. The second cell may be present in a concentration of more than 100 cells/ml in the sample. The second cell may be, for example, a leukocyte or an erythrocyte. The density and/or size of the second cell may be the same as or similar to that of the rare cell.

The particle may have a density or size which may cause a difference in density or size between the particle-rare cell complex and the second cell. For example, when the sample is blood including a cancer cell as a rare cell, the densities and diameters of leukocytes and erythrocytes are known in the art. The leukocytes have a density of 1.07-1.09 g/cm$^3$ and a wide range of diameters of 8-20 µm. The erythrocytes have a density of 1.1-1.15 g/cm$^3$ and a wide range of diameters of 6.6-7.5 µm.

The particle may be a polystyrene particle, polymethylmethacrylate particle, melamine particle, magnetic particle, latex particle, ABS (tert-polymer of acrylonitrile, butadiene, and styrene) particle, cyclic olefin copolymer particle, or a combination thereof.

The density of the particle may be varied depending on the rare cell and the sample. For example, when a circulating cancer cell is the rare cell to be separated from blood, the particle may have a density in a range of about 1.07 g/cm$^3$ to about 2.0 g/cm$^3$, about 1.07 g/cm$^3$ to about 1.9 g/cm$^3$, about 1.07 g/cm$^3$ to about 1.8 g/cm$^3$, about 1.07 g/cm$^3$ to about 1.7 g/cm$^3$, about 1.07 g/cm$^3$ to about 1.6 g/cm$^3$, about 1.07 g/cm$^3$ to about 1.5 g/cm$^3$, about 1.07 g/cm$^3$ to about 1.4 g/cm$^3$, about 1.07 g/cm$^3$ to about 1.3 g/cm$^3$, about 1.07 g/cm$^3$ to about 1.2 g/cm$^3$, or about 1.07 g/cm$^3$ to about 1.1 g/cm$^3$.

The diameter of the particle may be varied depending on the rare cell and the sample. The diameter may be the length of a straight line through the center of the particle. For example, when a circulating cancer cell is the rare cell to be separated from blood, the particle may have a diameter in a range of about 1 µm to about 6 µm, about 1.25 µm to about 5.5 µm, about 1.5 µm to about 5 µm, about 1.75 µm to about 4.5 µm, about 2 µm to about 4 µm, about 2.25 µm to about 3.5 µm, or about 2.5 µm to about 3 µm.

The density of the particle may be greater than the density of medium used in centrifugation. When a density gradient is used in the centrifugation medium, the density of the particle may be greater than the lowest density of the density gradient in the medium, such that the density of the particle falls within the range of densities of the density gradient. According to an exemplary embodiment, a density gradient medium has a density gradient ranging from about 1.077 g/cm$^3$ to about 1.30 g/cm$^3$, about 1.077 g/cm$^3$ to about 1.25 g/cm$^3$, about 1.077 g/cm$^3$ to about 1.20 g/cm$^3$, about 1.077 g/cm$^3$ to about 1.15 g/cm$^3$, or about 1.077 g/cm$^3$ to about 1.1 g/cm$^3$.

The moiety capable of binding to the rare cell may be any moiety that preferentially or specifically binds the rare cell over the second cell (e.g., binds to the rare cell to the substantial or total exclusion of the second cell). The moiety may be a ligand capable of binding to a surface protein, sugar, phospholipid, or cholesterol of the rare cell. The surface protein may be a protein specifically expressed in a cancer or tumor cell, for example, mucin 1 (MUC 1), topoisomerase IIa, epithelial cell adhesion molecule (EpCAM), c-Met, Her2, EGFR, E-cadherin, c-kit, endothelin-1, endothelin receptor-α, endothelin receptor-β, chemokine (CXC motif) receptor 4, breast cancer resistance protein, ABCA3, or any combination thereof. The moiety may be an antibody, enzyme substrate, enzyme inhibitor, lectin, phospholipid binding protein, cholesterol binding protein, or any combination thereof. The moiety is bound to the surface of the particle. For example, when the moiety is an antibody, the constant region of the antibody may be bound to the surface of the particle such that the antigen-binding site may be exposed to the outside. Accordingly, because the moiety bound to the particle binds specifically to a surface protein, sugar, phospholipid, or cholesterol of the rare cell, the particle may be bound specifically to the rare cell to permit separation of the particle-rare cell complex from the second cell.

The particle may be coated with a compound having a charge on the surface in order to permit binding to the moiety specific to the surface marker of the target cell. The compound having the charge may be a compound having a functional group of an amine group, an imino group, and any combinations thereof, but it is not limited thereto.

When the sample is incubated with the particle, the moiety bound to the particle may specifically bind to the surface protein, sugar, phospholipid, or cholesterol of the rare cell, but not to other cells (e.g. a second cell type) of the sample. For example, when an antibody specific for EpCAM and/or C-Met is used as the moiety, the moiety can specifically bind to EpCAM and/or C-Met on circulating tumor cells. Thus, the particle via the moiety binding to the surface protein, sugar, phospholipid, or cholesterol of the rare cell may form a complex with the rare cell. Due to formation of the complex, the overall density or size of the complex is altered compared to those of other cells in the sample, which have the same or similar density or size as the rare cell.

According to an exemplary embodiment, a ratio of sedimentation rate of the second cell to sedimentation rate of the complex may have a range of about 1:2 to about 1:30, about 1:2 to about 1:25, about 1:2 to about 1:20, about 1:2 to about 1:15, about 1:2 to about 1:10, or about 1:2 to about 1:5. The sedimentation rate is determined by Stokes' Law. Stokes' Law states that a particle moving through viscous liquid attains a constant velocity or sedimentation rate. The equation for Stokes' Law of Sedimentation is $v = d^2 (\rho_p - \rho_1)/18\eta \times g$, where v is the sedimentation velocity, d is the diameter of particle, $\rho_p$ is the particle density, $\rho_1$ is the density of the medium, $\eta$ is the viscosity of the medium, and g is the centrifugal force.

According to an exemplary embodiment, the density of the complex and the density of the second cell may differ by about 0.001 g/cm³ to about 0.2 g/cm³, about 0.001 g/cm³ to about 0.15 g/cm³, about 0.001 g/cm³ to about 0.1 g/cm³, or about 0.001 g/cm³ to about 0.05 g/cm³.

The method may include performing density gradient centrifugation with the incubated mixture to separate a fraction including the complex of the particle and the rare cell.

The complex of the particle and the rare cell may be separated from other components of the sample by centrifugation according to a sedimentation rate. The centrifugation may be accomplished by the any common method known to one of ordinary skill in the art. The portion of the centrifuged sample that does not include the complex of the particle and the rare cell may be removed.

Density gradient centrifugation may be performed with a gravitational force in a range of about 50 g to 650 g, about 60 g to 600 g, about 70 g to 550 g, about 80 g to 500 g, about 90 g to 450 g, about 100 g to 400 g, about 100 g to 350 g, about 100 g to 300 g, about 100 g to 250 g, about 100 g to 200 g, or about 100 g to 150 g.

The complex may be separated by isopycnic separation. Isopycnic separation involves adding a sample to a medium having a density gradient and then performing centrifugation. During centrifugation, the components of the sample travel through the gradient until they reach their respective isopycnic points, e.g., the point at which the density of a component equals the density of the medium. Therefore, isopycnic separation is carried out using a density gradient selected such that the density of particles in the sample falls within the range of densities in the gradient and irrespective of the gradient length. Sufficient centrifugation time should be given such that the various kinds of cells included in the sample, including the complex, may band to distinct layers at their isopycnic points. For example, centrifugation time may be about 30 sec to about 10 min, about 1 min to about 7 min, or about 2 min to about 5 min. Various media known in the art may be used at various concentrations, depending on the biological sample. For example, the medium may include sucrose, caesium chloride, Ficoll (a solution of high molecular weight sucrose polymers and sodium diatrizoate), Percoll (a solution of colloidal silica coated with polyvinylpyrrolidone), Nycodenz® (a solution of 5-(N-2, 3-dihydroxypropylacetamido)-2, 4, 6-tri-iodo-N, N'-bis (2, 3 dihydroxypropyl)isophthalamide), or combination thereof.

Since the complex has a sedimentation rate different from other cells in the sample, which have sedimentation rates similar or identical to that of the unbound rare cell, a layer of the complex may form separate from layers of the other cells in the sample. The layer or fraction of the gradient with the complex may then be extracted automatically or manually from the gradient.

The method may further include, after the performing density gradient centrifugation, determining the amount of the separated rare cell, for example, the number of separated rare cells. Determination of the amount of the separated rare cell may further include filtering the fraction including the complex of the particle and the rare cell to separate the complex from the fraction. The filtration may be accomplished using a filter, for example. The size of the complex of the particle and the rare cell is greater than the size of cells not part of a complex. Thus, the pore size of the filter may be greater than the diameter of the rare cells and smaller than the diameter of the complex. For example, the pore size may be the range of about 3 µm to about 30 µm, about 5 µm to about 25 µm, about 7 µm to about 20 µm, or about 9 µm to about 15 µm.

The method may further include analyzing the separated rare cell, a nucleic acid thereof, or a protein thereof. For example, the method may further include detecting the separated rare cells. Diseases including cancer may be diagnosed using the separated rare cells.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

Example 1

Manufacture of a Particle to which an Antibody Specifically Binding to EpCAM is Bound In a method of separating a target cell in a biological sample according to an exemplary embodiment, a breast cancer cell line MCF-7 (Korean Cell Line Bank) was used as a target cell to be separated. Accordingly, various kinds of commercially available antibodies were tested by flow cytometric analysis in order to select an antibody specifically binding to EpCAM in the target cell. As a result, a Human EpCAM/TROP1 Fluorescein monoclonal antibody MAb (Clone 158206), Mouse IgG2B (Cat. # FAB9601F, R&D Systems, Inc.: hereinafter "anti-EPCAM MAb") was selected (FIG. 1). The anti-EPCAM antibody was allowed to bind to the particle using the following method.

Amine-modified polystyrene beads (Sigma-Aldrich) or melamine beads (Postnova) having a diameter of about 2 µm to 3 μm were washed three times with phosphate buffered saline (PBS). Polymaleic acid having a carboxylic group activated with 1-ethyl-3(3-dimethylaminopropyl)carbodiimide/N-hydroxysuccinimide (EDC/NHS) was added to the beads and allowed to react with the beads at room temperature for about 1.5 hours while being stirred. Subsequently, the beads were washed three times with PBS buffer, and again activated with EDC/NHS while being slowly stirred at room temperature for 20 minutes, followed by reaction with about 625 ug/ml of anti-EPCAM MAb for about 1.5 hours to obtain polystyrene particles or melamine particles to which the anti-EPCAM MAb was bound.

Example 2

Agglutination Experiment Performed with the Particle to which Anti-EpCAM Mab is Bound and a Cancer Cell First, 20 μl of the polystyrene particles to which anti-EPCAM MAb is bound were added to a test tube. Then, 3 ml of blood including about 100 cells of the breast cancer cell line MCF-7 was added to the test tube and allowed react at room temperature for about 1 hour while being slowly stirred. The blood was from a normal patient, obtained in accordance with regulations of the Institutional Review Board at Yonsei University College of Medicine. Subsequently, particles showing fluorescence due to the fluorescein bound to the antibody were observed by using a fluorescent microscope (Olympus IX81). In addition, polystyrene beads without the antibody were used as a control in an experiment performed in the same manner.

Figure 2:
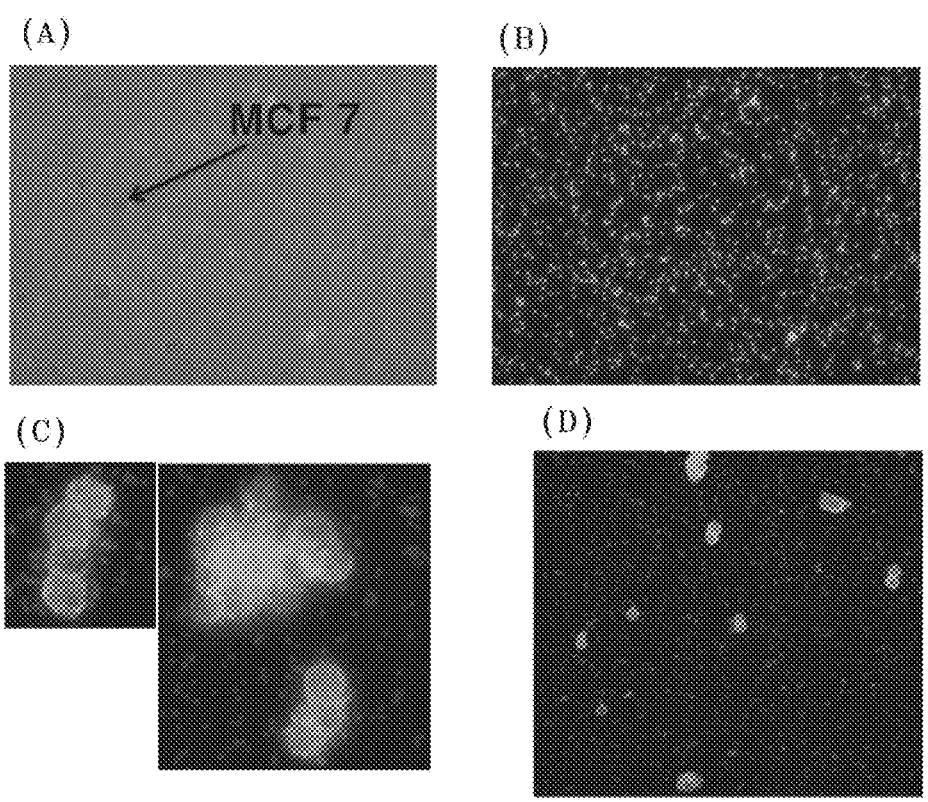
FIG. 2 is a set of images showing the results of agglutination reactions between a particle with bound anti-EPCAM MAb and a breast cancer cell line. Polystyrene beads without antibody were not bound to the breast cancer cells (FIG. 2A) and did not show any non-specific binding (FIG. 2B). In contrast, polystyrene beads with anti-EpCAM MAb were bound to the surface of the breast cancer cell (FIGS. 2C and 2D), as shown by the degree of fluorescence observed.

Results are shown in FIG. 2. Polystyrene beads without bound antibody were not bound to the breast cancer cells (FIG. 2A) and did not show any non-specific binding (FIG. 2B). In contrast, polystyrene beads with bound ant-EpCAM MAb were bound to the surface of the breast cancer cell (FIGS. 2C and 2D), as shown by the degree of fluorescence observed.

Example 3

Separation Experiment Performed on Cancer Cells in Blood Using Density Gradient Centrifugation Since white blood cells and circulating cancer cells are similar in terms of physical properties, it is known that they may separate in the same layer when density gradient centrifugation is performed. Accordingly, an experiment for separating only cancer cells in blood was performed in the present Example. The polystyrene particles with bound anti-EpCAM Mab were allowed to bind to cancer cells in the blood, producing a difference in density between the cancer cell-polystyrene particle complex and the white blood cells.

First, 4 ml of a normal patient's blood, obtained in accordance with regulations of the Institutional Review Board at Yonsei University College of Medicine, was added to a test tube and then spiked with 100 cells of the breast cancer cell line MCF-7. About 20 μl ($4.5 \times 10^8$ ea) of polystyrene particles with bound anti-EpCAM MAb were added to the test tube, and incubated for about 1 hour. Subsequently, about 3 ml of 100% Ficoll was injected into a 15 ml tube, to which the reaction was loaded, followed by centrifugation at 400×g conditions for about 20 minutes.

Figure 3:
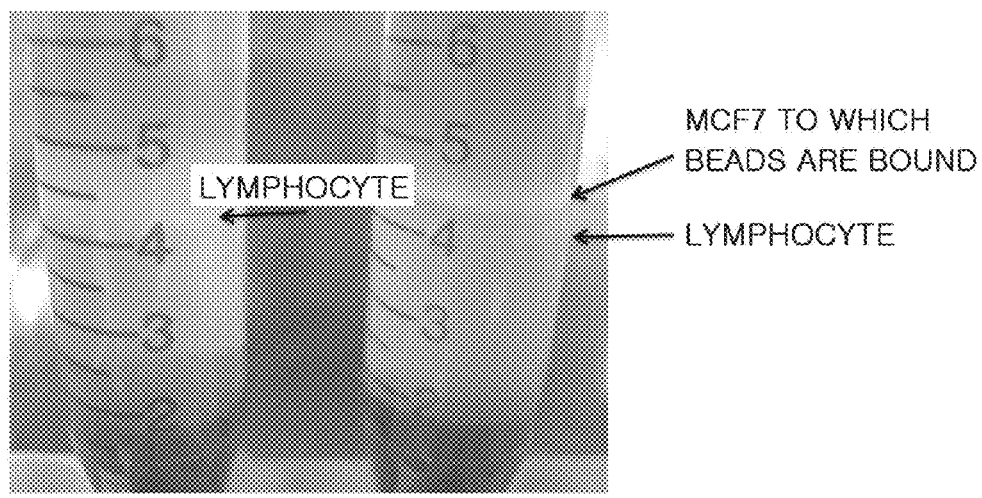
FIG. 3 is a photograph illustrating results of separation of cancer cells in blood by density gradient centrifugation.

As shown in FIG. 3, the cancer cells bound to the polystyrene particles with the bound anti-EpCAM MAb formed a layer in a portion of the density gradient formed during centrifugation above the layer of the lymphocytes. The density of the polystyrene particles used in the experiment was about 1.05 g/cm$^3$, which was a value lower than the density of lymphocytes (about 1.07 g/cm$^3$). Even though the number of the cancer cells in the blood sample was small, the cancer cells were separated from the lymphocytes due to the density of the polystyrene particles to which the cancer cells were bound. Thus, even when only a small quantity of the target cell is present in a biological sample, the method of separating the target cell from other cells in the sample, according to an exemplary embodiment of the invention, permits effective separation of the target cell.

Example 4

Separation Experiment Performed on Cancer Cells in Blood by Centrifugation and Filtration An experiment for separating only cancer cells in blood was performed in the present Example. The melamine particles with bound anti-EpCAM Mab were allowed to bind to cancer cells in the blood, separating the cancer cell-melamine particle complex from the white blood cells and the red blood cells by centrifugation and filtration.

First, 4 ml of a normal patient's blood, obtained in accordance with regulations of the Institutional Review Board at Yonsei University College of Medicine, was added to a test tube and then spiked with 100 cells of the breast cancer cell line MCF-7. About 100 ul ($1.0 \times 10^5$ ea) of melamine particles with bound anti-EpCAM MAb were added to the test tube, and incubated for about 1 hour. Subsequently, about 3 ml of Density gradient Ficoll Paque (Oslo) was injected into a 15 ml tube, to which the reaction was loaded, followed by centrifugation at 400×g conditions for about 10 minutes.

Figure 4:
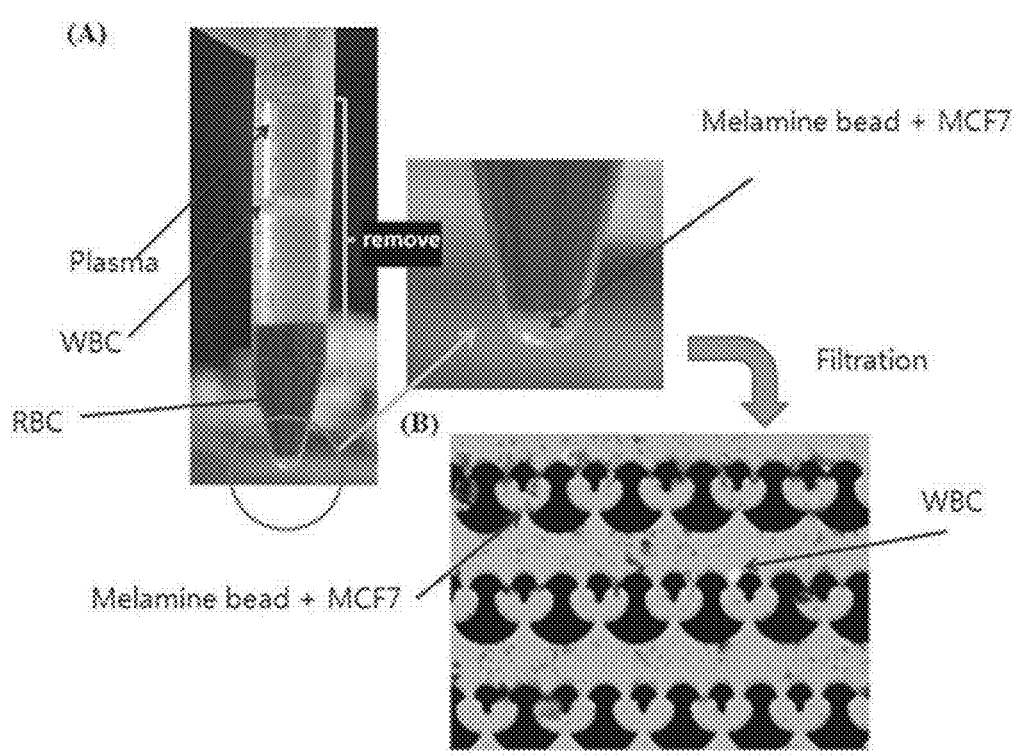
FIG. 4 is a photograph illustrating results of separation of cancer cells in blood by centrifugation and filtration.

As shown in FIG. 4A, the cells, such as the white blood cells or the red blood cells, which have lower density than the cancer cell-melamine particle complex were separated in the upper portion of the tube, whereas, the cancer cells bound to the melamine particles with the bound anti-EpCAM MAb were separated in the bottom end of the tube. The upper portion were removed, followed by the resultant were filtered using filter having 8-14 μm of the pore size. After the filtration, the filter was examined using fluorescent microscope (Olympus). As shown in FIG. 4B, it was identified that the cancer cell-melamine particle complex was easily separated by filtration because the complex was increased in size and density compared with other cells in the blood.

A target cell may be efficiently separated from a biological sample including at least one other type of cell which is similar in density to the target cell by the method of separating a target cell in a biological sample according to an exemplary embodiment disclosed herein.

Example 5

Relationship Between Separations of Cancer Cells from Blood and Sedimentation Rate of Centrifugation 1. Preparation of Size-Density Amplification Beads (SDABs)

SDAB was prepared with monoclonal anti-human EpCAM/TROP1 antibody (R&D Systems, MN) using standard carbodiimide chemistry in a single reaction. Briefly, the magnetic protein G (pG) modified microbeads (Invitrogen, CA) were washed with 1 mL of NaOAc buffer at pH 5.6 three times and mixed with 100 μg of monoclonal anti-human EpCAM/TROP1 antibody. The reaction container was kept in rotation at 12 rpm for over 1.5 h at room temperature on a rotator (PTR-60, Grant-bio, Shepreth, U.K.). After the beads were collected, dimethyl phthalate (DMP) (Sigma-Aldrich, MO) as a cross-linking agent was added and mixed at room temperature for 1 h. The reaction was stopped by the addition of 50 mM ethanolamine. The resulting beads were then washed three times with PBS buffer at pH 7.4, followed by blocking with 5% BSA for 2 h at room temperature. Finally, the beads were resuspended and stored in 1% bovine serum albumin (BSA). The obtained microbeads include protein G (pG) and anti-human EpCAM/TROP1 antibody.

2. Separation of Cancer Cells from Blood

A total of 100 cells of breast cancer cell line MCF-7 (ATCC) and small cell lung cancer dell line DMS-79 (ATCC) were introduced into a tube with 1 mL of whole blood sample, followed by the addition of 40 μL (2.0×10⁹/mL) of SDABs. The entire tube was incubated for 1.5 h at room temperature, while constantly being rotated at 12 rpm. Then, 1 mL of preincubated blood samples were carefully layered onto 2 mL of Ficoll-Hypaque gradient medium (1.077 g/mL). The blood-cell mixture was centrifuged with a centrifuge (Eppendorf 5810 R, Hamburg, Germany).

After centrifugation at a given g force, 2 mL of the upper layer (leukocytes with erythrocyte-concentrated fraction) was carefully aspirated and discarded. About 1 mL of the residual sample was resuspended with a pipet and transferred to the filtration device with 10-14 μm of slot width which was fabricated by silicon-on-glass (SOG) technology to make an accurate and precise gap between filter slots. The liquid in the blood samples was drawn through the filter, using a syringe pump (KDS LEGATO 110, KD Scientifc Inc., New Hope, Pa.), at a specific flow rate of buffer. After this initial filtration, cells trapped in the microfilter device were washed with 2 mL of PBS buffer at a flow rate of 100 μL/min. Prior to any immunostaining, cell fixation was conducted with 4% paraformaldehyde through the microfilter for 20 min at a flow rate of 50 μL/min. Cells were then permeabilized in 0.01% Triton X-100 (Sigma-Aldrich, MO) for 10 min at a flow rate of 50 μL/min. To identify CTCs and leukocytes, the mixture of DAPI, anti-cytokeratin-PE antibody, and anti-CD45-FITC antibody was flowed through the filter at 7.5 μL/min for 60 min. Finally, the microfilter was washed with PBS at a flow rate of 50 μL/min for 10 min. Cancer cells were imaged by a fluorescence microscope (1×81, Olympus Corp., Japan), integrated with a computer-operated motorized stage (TANGO, Märzhäuser Wetzlar GmbH & Co. KG, Germany).

3. The Effects by the Size and Density of SDABs on Separation of Cancer Cells from Blood As the size and density of beads was changed, efficiencies of separation of cancer cells from blood were calculated.

To calculate the sedimentation rate of cells, such as leukocytes, erythrocytes, and cancer cell-SDABs, at a given g force from Equation 1, it is assumed that cancer cells have diameters between 10 μm and 24 μm and a uniform density of 1.07 g/cm³. It is also assumed that cell surfaces are fully covered with SDABs. For leukocytes and erythrocytes, it is assumed that leukocytes have a 20 μm diameter and a density of 1.09 g/cm³ and erythrocytes have a 7.5 μm diameter and a density of 1.15 g/cm³.

The sedimentation rate was calculated from the following Equation 1:

$$v = \frac{d^2(\rho_p - \rho_1)}{18\eta} \times g \qquad [\text{Equation 1}]$$

(v: sedimentation rate, d: diameter of particle, $\rho_p$ particle density, $\rho_1$: density of the density gradient medium, $\eta$: viscosity of the density gradient medium, g: centrifugal force)

Figure 5A:
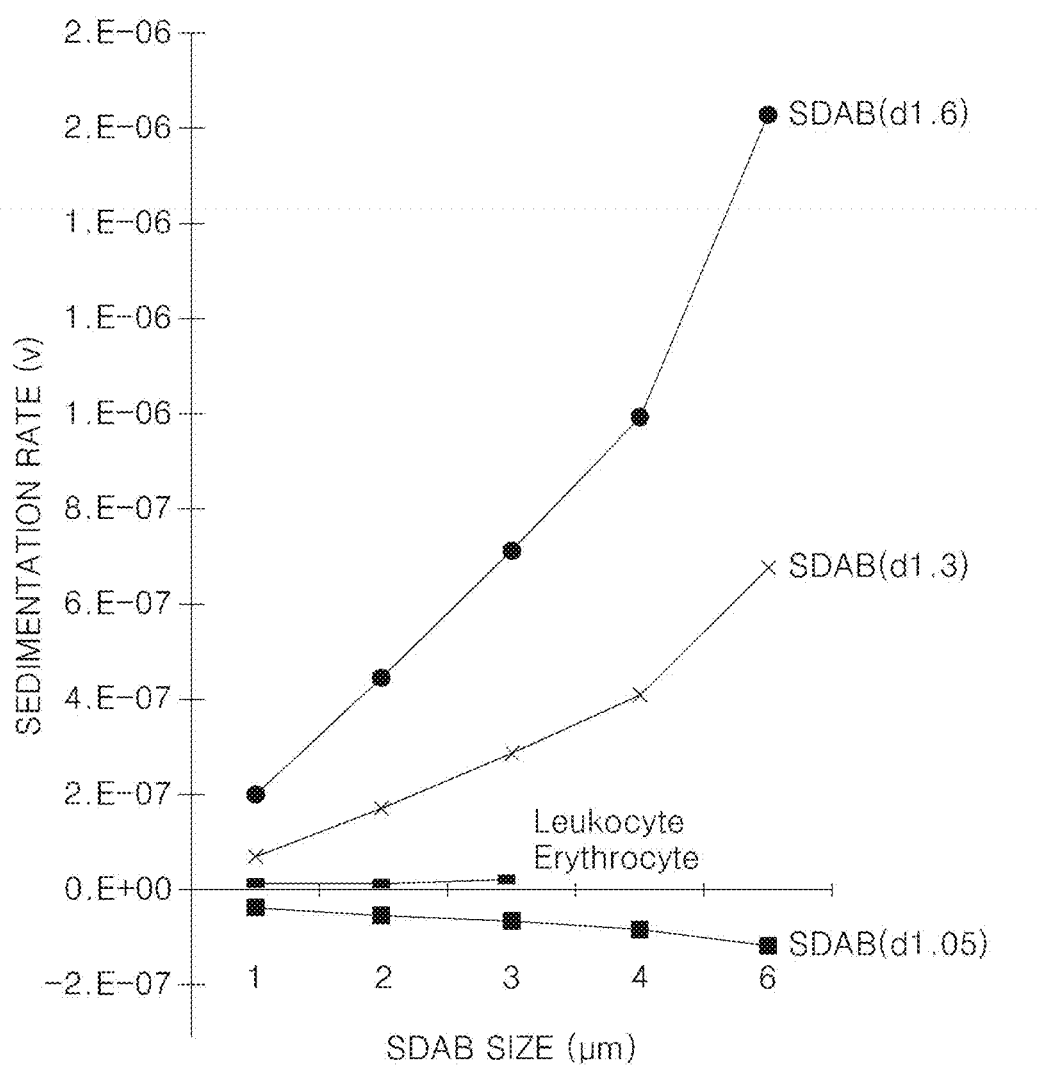
FIGS. 5A and 5B are graphs showing the calculated sedimentation rate.

As is shown in FIG. 5A, cells conjugated to SDAB with a density of about 1.05 g/cm³ cannot settle out of a blood suspension, because cell-SDABs complexes is lower in density than the gradient medium (d=1.077 g/cm³). However, sedimentation rates increased dramatically, when the density of SDAB was increased from about 1.3 to about 1.6 g/cm³. In addition, the sedimentation rate of cell-SDABs complex increased when the diameter of SDAB was increased from about 1 to about 6 μm, since both the diameter and the density of cell-SDABs complex correlates positively with the diameter of SDAB, given that the density of SDAB is greater than that of density of the gradient medium. Thus, to maximize the difference in sedimentation rates between cell-SDABs complex and leukocytes, SDAB should have a high density and large size. However, as large microbeads (diameter, 6 μm) showed poor binding efficiency to tumor cells, the optimal diameter of SDAB for use in our selective sedimentation assay was determined to be about 2.8 μm.

Figure 5B:
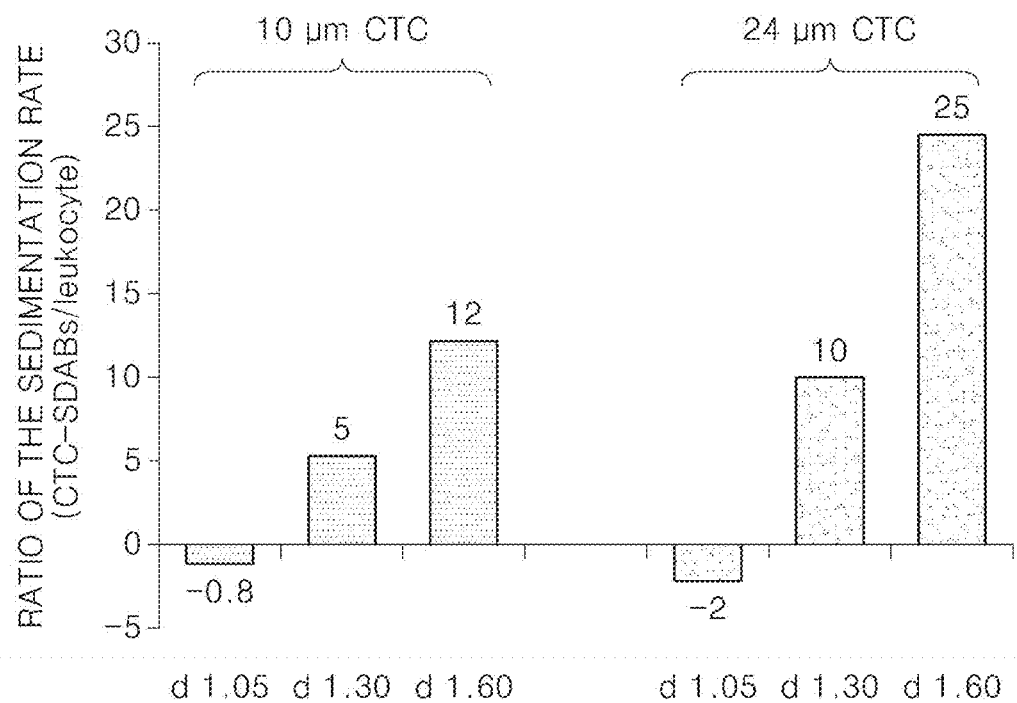

As is shown in FIG. 5B, the ratio of sedimentation rates between cell-SDABs and leukocytes was calculated. The term "d" in the figure refers to the density of the SDAB. The sedimentation rate of the cells (diameter, 10-24 μm) conjugated with 2.8 μm diameter SDABs of density ranging from about 1.3 to about 1.6 g/cm³ was about 5-25 times higher than that of leukocytes.

4. The Effects by the Number of SDABs Bound to the Cell on Separation of Cancer Cells from Blood It was investigated how much of the cell surface has to be covered by SDABs in order to separate cancer cell-SDABs complex from blood cells. For binding cells and SDABs, the actual number of cells in the cell suspension was determined by the cell counting method.

Figure 6A:
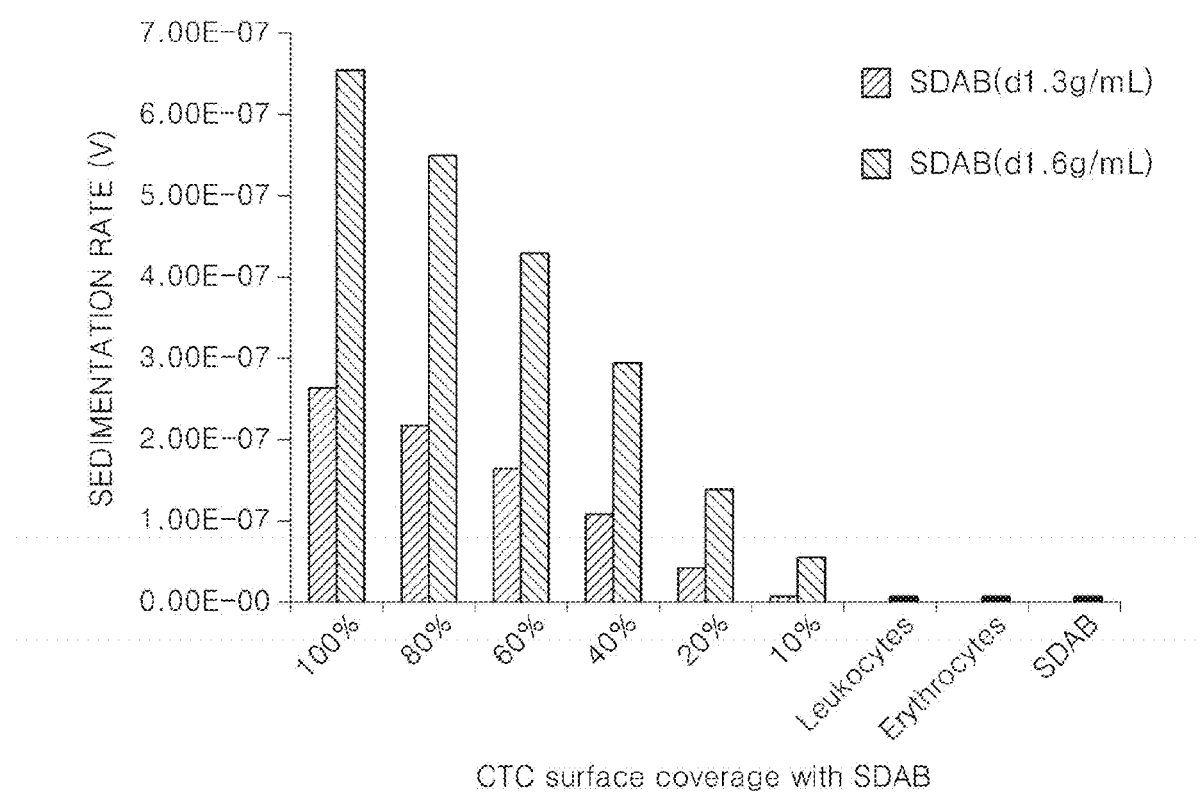
FIG. 6A is a graph showing sedimentation rates versus CTC surface coverage with SDAB when the CTC has a 24 μm diameter.

As is shown in FIGS. 6A and 6B, the sedimentation rate was different between cell-SDABs complex and blood cells if greater than 10% of the surface of a cancer cell is covered by SDAB. This corresponds to about 4 beads for a cancer cell with a diameter of 10 μm.

5. The Effects by the Centrifugal Force on Separation of Cancer Cells from Blood To verify the effects by the centrifugal force on separation of cancer cells from blood, various centrifugal forces ranging from 10 g to 800 g were applied for 2 min. After the centrifugation, the cells in the obtained fraction were detected. Most erythrocytes and leukocytes were found in the uppermost layer, while the lowermost layer contained cancer cell-SDABs precipitated to the bottom of the container after centrifugation at less than 200 g. However, at centrifugal forces greater than 200 g, more erythrocytes began to be found in the lowermost layer, reaching a complete lack of layer separation at centrifugal forces greater than 400 g.

To recover and evaluate the fraction of the settled cancer cells bound with SDABs, about 2 mL of the upper layer, containing leukocytes and erythrocytes, was removed, and the bottommost about 1 mL of remaining blood sample was obtained as a cancer cells fraction. The cancer cells fraction was directly injected into an inlet hole of the microfilter chip by applying negative pressure. The microfilter chip had a filter slot of width 10 μm. Subsequently, reagents for washing and staining were serially injected into the microfilter chip for optical inspection via fluorescence microscopy. To identify and count the entrapped cells, whole cellular images were obtained. Recovered cells that were DAPI-positive, CK-positive, and CD45-negative were identified as tumor cells, and cells that were DAPI-positive and CD45-positive were identified as leukocytes. The control samples were not treated with selective sedimentation. Recovery rate was defined as percentage of recovered cancer cells, found optically on the filter, divided by the total number of cancer cells input.

Figure 7A:
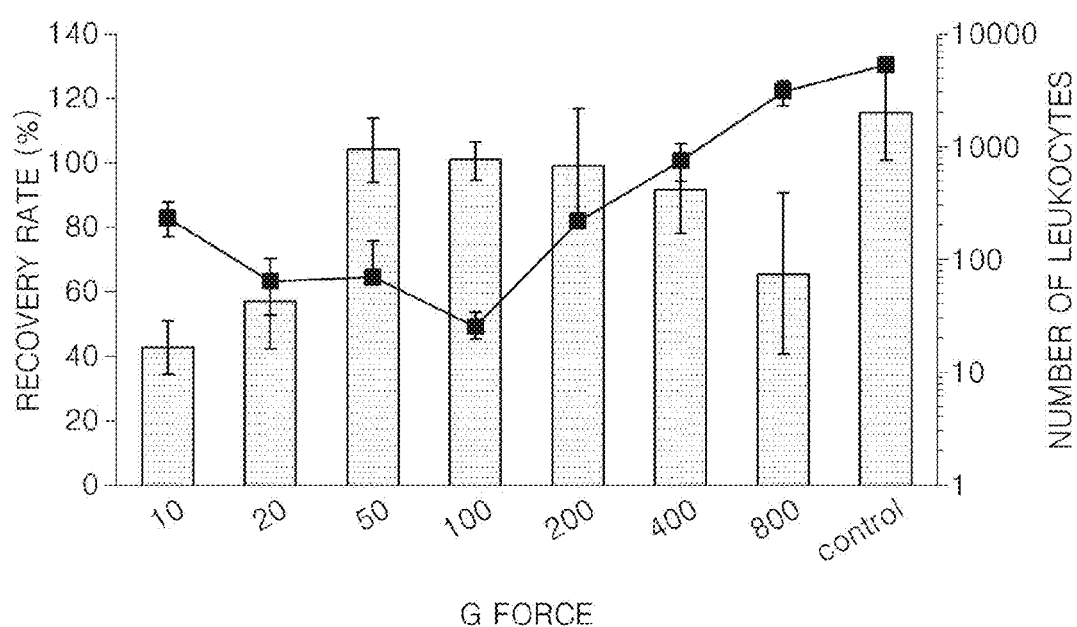
FIG. 7A is a graph showing recovery rates at different g forces.

As shown in FIG. 7A, the recovery rates were very good when the g force applied was in the range of about 50 g to about 100 g and the numbers of leukocytes were less than 100 cells. However, poor recovery rates were observed in cases where the centrifugal force was less than about 20 g or greater than about 800 g. Furthermore, the number of leukocytes, optically identified in the filter, dramatically increased at g forces greater than about 200 g.

Figure 7B:
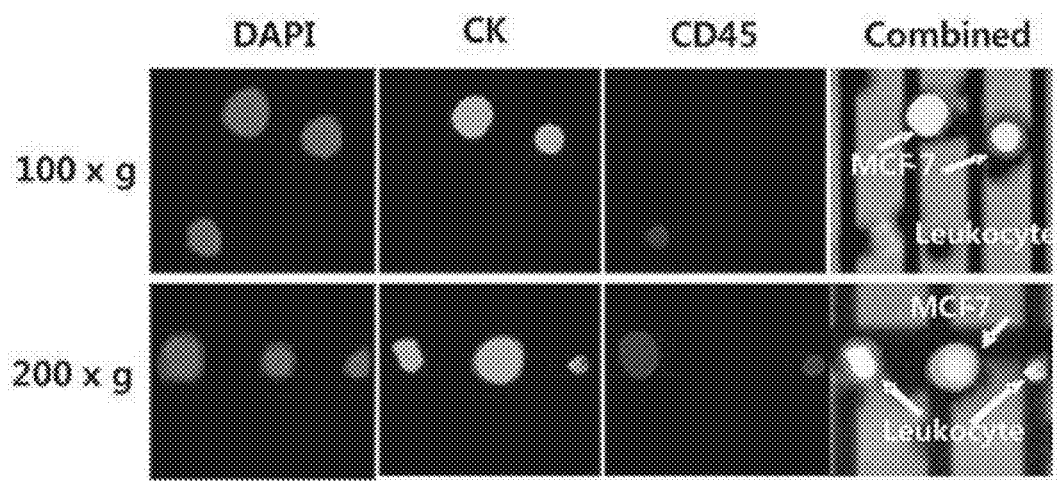
FIG. 7B is an image showingfluorescence of cancer cells (MCF-7) captured on the microfilter.

As shown in FIG. 7B, cancer cells were identified by DAPI-positive, CK-positive, and CD45-negative expression, when visualized by fluorescence microscopy. However, in some cases, a large number of triple positive cells (DAPI-positive, CK-positive, and CD45-positive) were observed at centrifugal forces greater than about 200 g.

Therefore, the optimal centrifuge conditions for selective sedimentation were determined to be about 100 g for about 2 min with a suspension height of 3 cm to 4 cm, considering both the recovery rate for cancer cells and the final removal rate of leukocytes. As a result, the removal efficiency of erythrocytes and leukocytes after the selective sedimentation step were about 99.81% and about 99.996%, respectively. After filtration the recovery rate for cancer cell was about 103±6% (n=4) and the total removal efficiency was determined to be about 99.9995% based on the leukocyte starting from about $9.5 \times 10^6$ and finally observed as less than about 50±7 cells (n=4).

Example 6

Relationship Between Separations of Cancer Cells from Blood and Conditions of Filtration 1. The Effects by Flow Rate of Buffer for Washing on Separation of Cancer Cells from Blood In order to demonstrate the effect that flow rate may have on tumor cell recovery rate and leukocyte removal efficiency, the cancer cell fractions obtained by selective sedimentation assay were passed through the microfilter device with a slot width of 10 μm at flow rates ranging from 50 μL/min to 2000 μL/min, after being subjected to the optimal g force of 100 g for 2 min.

Figure 8:
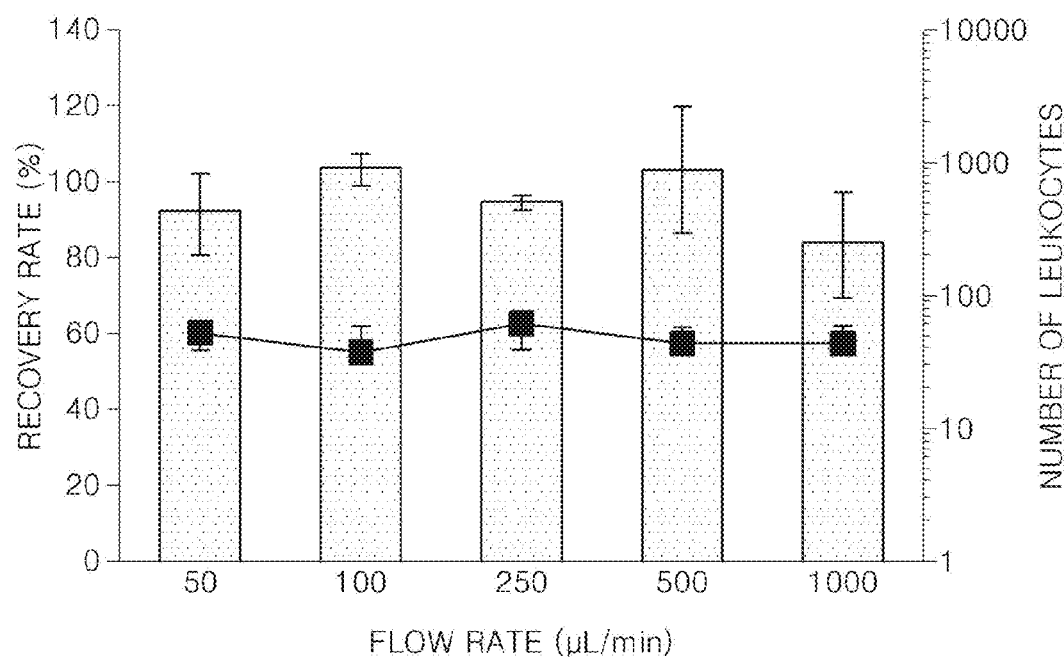
FIG. 8 is a graph showing the effect of the flow rate of buffer for washing in filtration on MCF-7 cell recovery rate (gray bars) and the number of captured leukocytes (■).

As shown in FIG. 8, recovery rates were decreased from about 107±4.6% (n=3) at 100 μL/min to about 84±13.3% (n=3) at 1000 μL/min. The standard deviation for recovery rates was significantly increased at flow rates greater than about 500 μL/min, while the number of leukocytes remained constant at various flow rates, with a high purity of less than about 50 cells at all flow rates tested.

Therefore, the optimal flow rate was determined to be about 100 μL/min, since this flow rate maximizes the recovery rate, while minimizing variation within the recovery rates.

2. Relationship of Recovery Rate Between Size of Cancer Cells and Filter Slot Width As the filter slot width is changed, recovery rate of small size DMS-79 cells and large size MCF-7 cells were calculated.

Figure 9A:
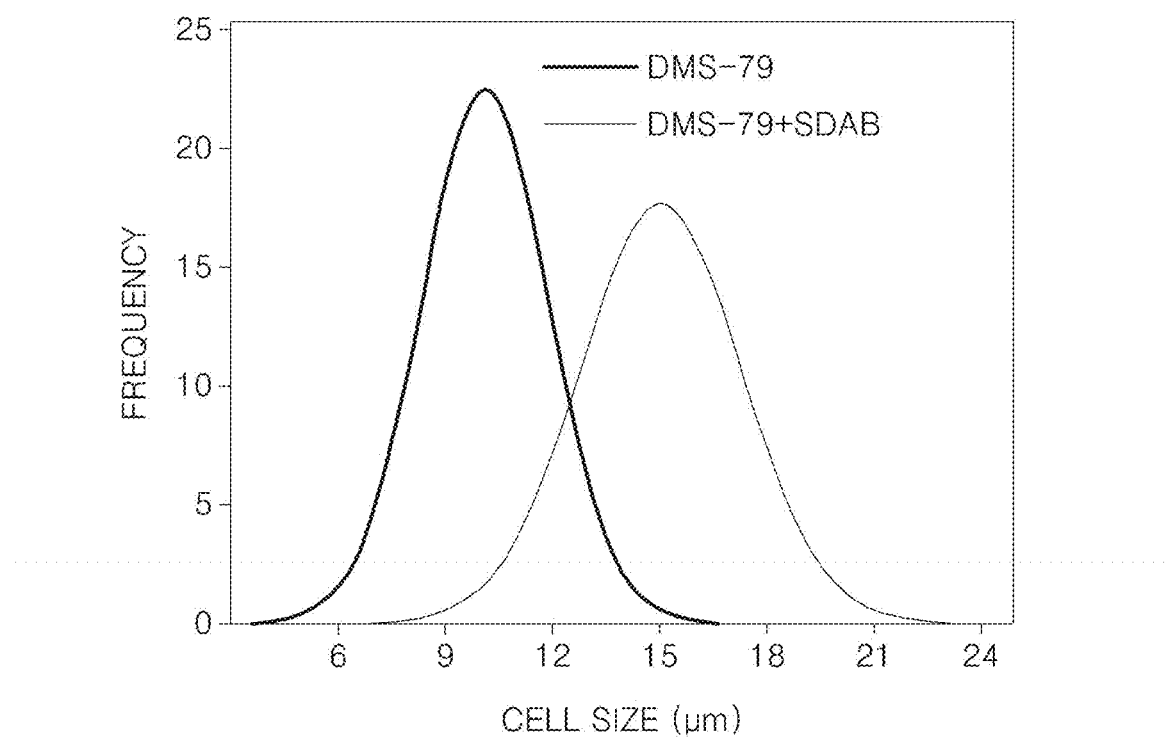
FIG. 9A is a graph showing a size distribution of original DMS-79 cells (black line) and DMS-79 cells with SDABs (red line).

As shown in FIG. 9A, control DMS-79 cells and DMS-79 cells with attached SDABs show a distribution in diameter from 7 to 19 μm (n=100, mean; 10 μm diameter, ±1.8 μm) and from 11 to 24 μm (n=100, mean; 15 μm diameter, ±2.2 μm), respectively. The recovery rates for MCF-7 and DMS-79 cells were compared at filter slot widths of 10, 12, and 14 μm. Unlike MCF-7 cells, which greatly overexpress EpCAM, to enhance the binding efficiency between DMS-79 cells and SDABs, plasma was removed from whole blood, prior to incubation with antibody-conjugated beads.

Figure 9B:
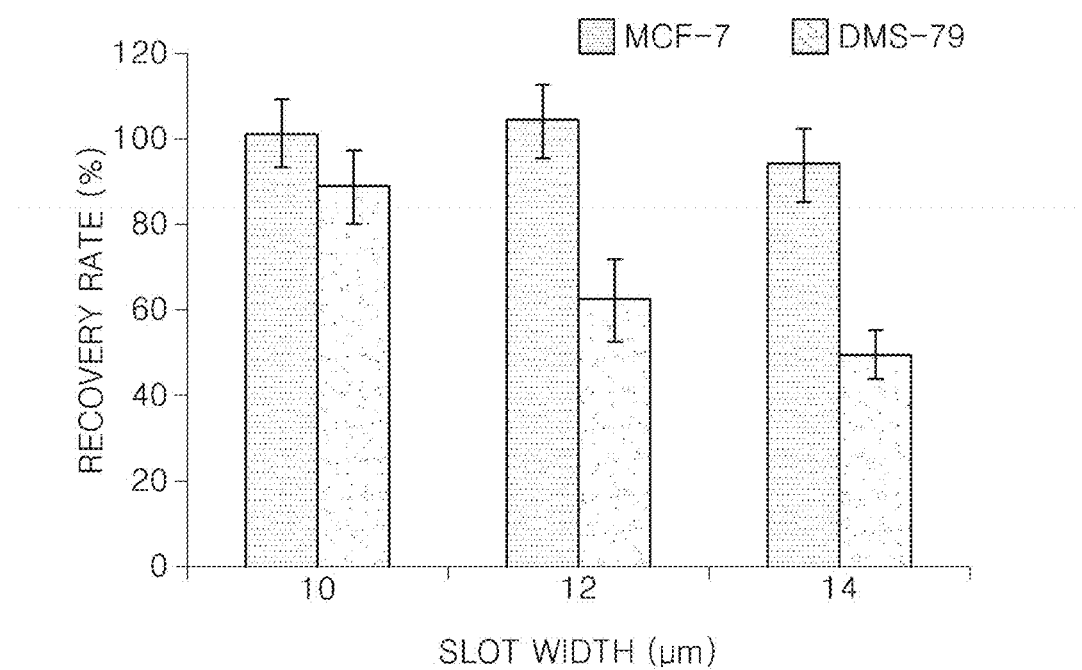
FIG. 9B is a graph showing recovery rates of tumor cells, as a function of slot width of the micro filter. MCF-7 and DMS-79 cells were spiked into whole blood at 100 cells/mL.

As shown in FIG. 9B, size amplified DMS-79 cells showed recovery rates of about 89±8% (n=3) at a slot width of 10 μm. As the slot width was increased from 10 to 14 μm, the recovery rate for DMS-79 cells decreased significantly to about 49±6% (n=3), whereas the recovery rate for MCF-7 cells remained constant at about 100±5%. The number of leukocytes detected on the microfilter did not exceed 50 cells at the most narrow slot width, where the highest number of leukocytes is expected. Therefore, it is demonstrated that small cancer cells, as well as large cancer cells, can be efficiently recovered and detected in a microfilter (slot width of 10 μm) with high purity because selective sedimentation, prior to filtration, had already removed a great number of leukocytes.

3. Assessment of Sensitivity in Recovery Rates

To validate sensitivity in recovery rates for cancer cells in blood, a series of blind spiking studies were performed using MCF-7 breast cancer cells. A series of MCF-7 cell-spiked blood samples were prepared by introducing 5 (±1.6), 10 (±3.3), 25 (±4.4), 50 (±6.3), or 100 (±8.5) MCF-7 cells to 1 mL of whole blood. The number of input cells was controlled as before, by serial dilution and verification of this dilution through five independent manual counts through visualization with an optical microscope. Assessment of sensitivity showed that it is detectable to MCF-7 cancer cells at concentrations as low as 5 cancer cells per 1 mL of blood.

Figure 10:
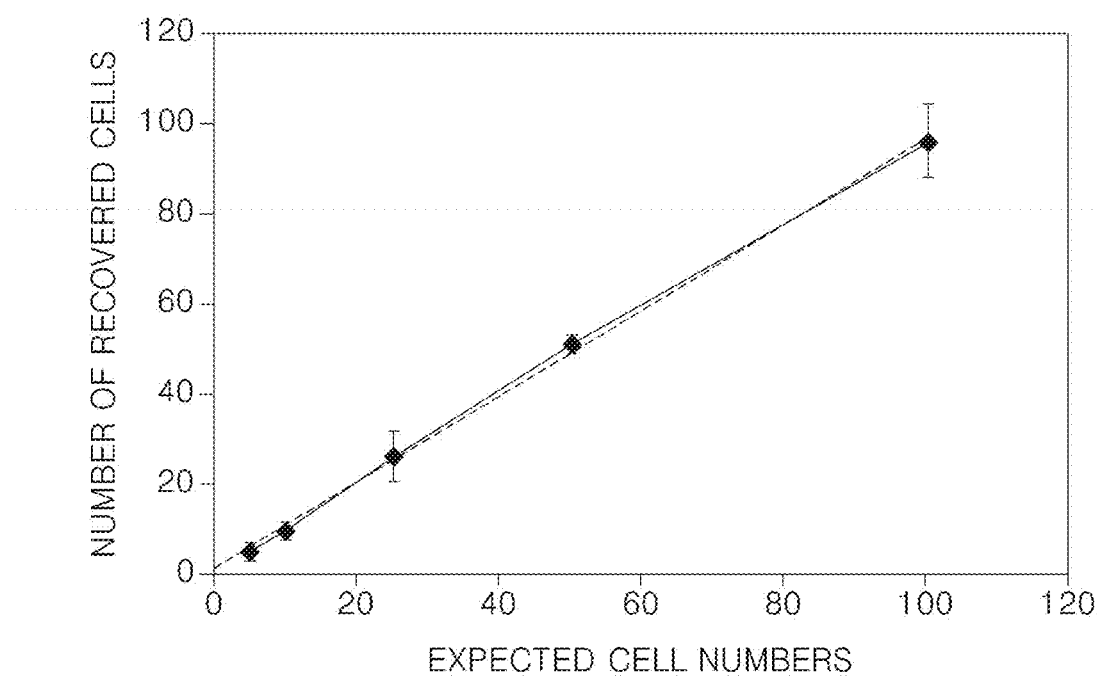
FIG. 10 is a graph showing sensitivity of the cancer cell detection at various tumor cell concentrations (dot line: spiked cell number, solid line: recovered number of cells).

As shown in FIG. 10, the recovery rate was found to be the 99±4% (n=15) when 5-100 MCF-7 cancer cells were present in 1 mL of blood. As shown in FIG. 10, a linear regression model showed good correlation between the number of observed cells and the number of expected cells, i.e., the number of input cells (adjusted $R^2$=0.987, P<0.05).

The terminology used herein is for the purpose of describing particular embodiments only and is not intended to be limiting of the invention. The terms "a" and "an" do not denote a limitation of quantity, but rather denote the presence of at least one of the referenced item. The terms "comprising", "having", "including", and "containing" are to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. No language in the specification should be construed as indicating any non-claimed element as essential to the practice of the invention as used herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. An improved method of separating a circulating tumor cell (CTC) from a sample, the improvement comprising
   specifically binding the CTC to a particle and centrifuging the sample so as to effect a differential centrifugation rate:
   incubating a sample comprising a CTC and a leukocyte with a particle comprising a moiety that selectively binds to the CTC to form a complex comprising the particle and the CTC; and,
   centrifuging the sample in a centrifugation medium to separate the complex from the leukocyte;
   wherein the complex and the leukocyte exhibit a sedimentation rate during centrifugation, and the ratio of the sedimentation rate of the leukocyte to the sedimentation rate of the complex is about 1:2 to about 1:30,
   wherein the density of the particle is about 1.07 g/cm3 to about 2.0 g/cm3,
   wherein the diameter of the particle is about 1 μm to about 6 μm,
   wherein the centrifuging is performed with a gravitational force of about 50 g to about 200 g.

2. The method of claim 1, wherein the density of the leukocyte and the density of the complex differ by about 0.001 g/cm$^3$ to about 0.2 g/cm$^3$.

3. The method of claim 1, wherein the centrifugation medium has a density gradient prior to centrifugation, and the particle has a density greater than the lowest density of the centrifugation medium.

4. The method of claim 1, wherein the sample is combined with a centrifugation medium having a density gradient prior to centrifugation, and in the density gradient has a density range of about 1.077 g/cm$^3$ to about 1.30 g/cm$^3$.

5. The method of claim 3, wherein the medium comprises caesium chloride, sucrose, sucrose, cesium chloride, a solution of high molecular weight sucrose polymers and sodium diatrizoate, a solution of colloidal silica coated with polyvinylpyrrolidone, a solution of 5-(N-2, 3-dihydroxypropylacetamido)-2, 4, 6-tri-iodo-N, N'-bis (2, 3 dihydroxypropyl) isophthalamide, or a combination thereof.

6. The method of claim 1, wherein the centrifuging is performed with a gravitational force of about 50 g to about 100 g.

7. The method of claim 1, wherein the CTC is a cell derived from blood, marrow fluid, saliva, lachrymal fluid, urine, semen, mucous fluid, or any combination thereof.

8. The method of claim 1, wherein the moiety that selectively binds to the CTC is an antibody, enzyme substrate, enzyme inhibitor, lectin, phospholipid binding protein, cholesterol binding protein, or any combination thereof.

9. The method of claim 1, wherein the particle is a polystyrene particle, polymethylmethacrylate particle, melamine particle, magnetic particle, latex particle, ABS (tert-polymer of acrylonitrile, butadiene, and styrene) particle, cyclic olefin copolymer particle, or a combination thereof.

10. The method of claim 1, further comprising determining the amount of the separated CTC.

11. The method of claim 10, wherein determining the amount of the separated CTC further comprises filtering a fraction of the centrifugation medium containing the complex to separate the complex.

12. The method of claim 1, further comprising analyzing the separated CTC, a nucleic acid thereof, or a protein thereof.

13. The method of claim 1, further comprising separating the CTC from the particle.

* * * * *